(12) United States Patent
Kim et al.

(10) Patent No.: US 6,958,434 B2
(45) Date of Patent: Oct. 25, 2005

(54) OSCC1 PROMOTER AND METHODS OF TRANSFORMING MONOCOT PLANTS USING THE SAME

(75) Inventors: Ju-Kon Kim, Kyunggi-do (KR); Beak-Hie Nahm, Kyunggi-do (KR); Sang-Ik Song, Kyunggi-do (KR); In-Cheol Jang, Kyunggi-do (KR); Won-Bin Choi, Seoul (KR); Kyung-Hee Lee, Seoul (KR)

(73) Assignee: Greengene Biotech, Inc., Kunggi-do (KR)

( * ) Notice: Subject to any disclaimer, the term of this patent is extended or adjusted under 35 U.S.C. 154(b) by 68 days.

(21) Appl. No.: 10/129,458

(22) PCT Filed: Oct. 25, 2001

(86) PCT No.: PCT/KR01/01807

§ 371 (c)(1),
(2), (4) Date: May 30, 2003

(87) PCT Pub. No.: WO03/038102

PCT Pub. Date: May 8, 2003

(65) Prior Publication Data

US 2004/0187174 A1 Sep. 23, 2004

(30) Foreign Application Priority Data

Oct. 8, 2001 (KR) .......................... 2001-61935

(51) Int. Cl.$^7$ .......................... C12N 15/82; C12N 15/11
(52) U.S. Cl. ...................... 800/278; 536/24.1
(58) Field of Search ............... 800/278, 279, 800/293, 294; 526/24.1; 536/24.1

(56) References Cited

PUBLICATIONS

Wing et al, 2000, GenBank Accession No. AZ131495.*

* cited by examiner

*Primary Examiner*—Anne Kubelik
(74) *Attorney, Agent, or Firm*—Nath & Associates PLLC; Harold L. Novick

(57) ABSTRACT

The present invention relates to a process for varying a trait of monocot plants, wherein the process comprises the step of transforming a monocot plant with a recombinant plasmid containing an OsCc1 promoter and a desired nucleic acid.

5 Claims, 4 Drawing Sheets

SEQUENCE LISTING

<160> NUMBER OF SEQ ID NOS: 3

<210> SEQ ID NO 1
<211> LENGTH: 1882
<212> TYPE: DNA
<213> ORGANISM: Oryza sativa

<400> SEQUENCE: 1

```
gaattcggat cttcgaaggt aggctgcagt tcttgaattg ttgaattatt attatcttca      60
tcttcattca tctgtaacta ctgattcatc tggtttgtta ttaccgatcg taatgccgtt     120
gttttgtcaa aaaaaaaaaa ggagatcggt ttgttattac cgatcataat gctgttcttt     180
tataaaaaaa aaacatggat ctattggcat aatcttttg cgccaggtac tccgaccatt      240
actcggttac cgacgaaagc cggtgagatt tggataaact tcgccaaaaa tttaaatttc     300
cgtttgatct ctcaaacgtg ggctggttta ggcctgttta atgtttagac acatgtatgg     360
agtactaaat attaataaaa aaataatta cacagatcgt gtgtaaattg cgagataaat      420
cttttaagcc taattgctcc atgaacaatg tggtgttaca gtaaacattt gctaatgaca     480
gattaattag gcttaataaa ttcgtctcac agtttacagg tgaaatatgt aatttattta     540
ttattaagtc tatatataat actttaaata cgtgaccgta tcccgatgg ggagacacgt      600
aaaactttt aaccaagttc taaacacaac cttgcttcac agtttcttga tctctatggg      660
tagggtggg cagaaaaaga ccgaaccgaa agaccgaacc gaaaaggccg agaccgagac      720
cgaaaagatc gagaccgaga aattcggtcc taggtaatga aagaccgaat tttgttcggt     780
caatttggtt agttttctcg ggtaaccgaa tagaccgaaa agaccaaatt atcagaaaat     840
atctaaatac aatctacaac ccactatgtt taataggatt aaactctaat tttttacatc     900
cctacttctt ttaggcatgc aacctaataa gagtctttac tcataagtgc ttacgaaatt     960
tttttgtgat ttttgtgttg aaaatttcca ttatttcttt gcatatatga aatgttgtt     1020
gaatttcggt caggaccgag accgagactg aatttgtcag tcctaacatt ttttcaccga    1080
aattcagtct tcacttttca aagactgaaa agaccgaaag actgaagacc gagaccgaaa    1140
ttttcggtta gaccgaatgc ccaccccctat ctacgggctt gataagatca ataaccgtaa    1200
ttaccgaagc ggttgcgtga cttgctgttg catttgtcaa ccctaacata gtactacctc    1260
cgtttcaagg ttccgtttca gagtttgtaa actttccta gtattaaccc atgttttaac    1320
ttgcaacggg aggaagttaa catcctatac gcctgaaatc cctttaaaaa aaaagaacat    1380
ttatacgctg gaaccgattc tgaaccggtc cgtccaccca ccgacccacc aacggtgcga    1440
tttccaccgt ccaccaaacg cgagccgcct ccaccctcca cctatcgagt caaagacgac    1500
gactctacca gagcacgtgg acccggtcca cgaacggaac gcccttacac cgaatgggcc    1560
gttgggtgtc cacgcctccc acaccacac cccccttgcc tttttctgca agacacggaa    1620
accttctgga accgcgtgga ttccccgaaa cgccctgcc ccacgctcc acccgttcaa     1680
taattctagg ggtattatcg tagtttcgcc acctgcccctt ccgccgcgct ggtgtatact   1740
agggcacgcg ctcctcggaa tcgccacgag cccacgagcc agaaaaaaaa ggaaaaaaag   1800
agagtcgtag ttcgcctctt cttcctcctc tcgttctcgc ggcggcggcg gagatggcgt   1860
cgttctcgga ggctccccccg gg                                           1882
```

<210> SEQ ID NO 2
<211> LENGTH: 32

```
-continued

<212> TYPE: DNA
<213> ORGANISM: Artificial Sequence
<220> FEATURE:
<223> OTHER INFORMATION: primer

<400> SEQUENCE: 2
aactggagga attcggatct tcgaaggtag gc                              32

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
aaccatggcc gccgccgccg cgagaacg                                   28
```

US 6,958,434 B2

OSCC1 PROMOTER AND METHODS OF TRANSFORMING MONOCOT PLANTS USING THE SAME

FIELD OF THE INVENTION

The present invention relates to a process for varying a trait of monocot plants, which comprises steps of transforming a monocot plant with a recombinant plasmid containing OsCc1 promoter for transformation of monocot plants and a desired foreign gene and of expressing said foreign gene.

BACKGROUND THE INVENTION

In producing farming plants having novel characteristics, which can develop an agricultural field, expression of a foreign gene (i.e., transgene) to be introduced into a plant body is greatly influenced by transcriptional, post-transcriptional, translational and post-translational elements. Among said elements, particularly, a promoter belonging to the transcriptional elements is the most important element, which not only can directly influence a transcription of a transgene to ultimately change the expression level, but also can change the steps of expressing a transgene, or the tissue- or cell-specificities. To date, although numerous promoters have been isolated from various plants for expression of a trangene, only a few promoters among them are currently practically used for transformation of a plant body. CaMV (cauliflower mosaic virus) 35S promoter and its derivatives, which have been most widely used in this field at present, induce an extensive expression of genes in the whole tissues of a plant body and, exhibit a high activity especially in vascular tissues and most cells of roots and leaves. However, the CaMV 35S promoter exhibits lower activity in monocot plants such as rice plant, etc., than in dicot plants, and even does not exhibit any activity in certain cells such as pollen, etc. Numerous promoters other than CaMV 35S promoter, which have originated from dicot plants, have also been used for transformation of monocot plants, but exhibit lower activity than do promoters originating from monocot plants. Further, rbcS (ribulose bisphosphate carboxylase/oxygenase small subunit) promoter of rice plant, Act1 (actin1) promoter of rice plant, and Ubi1 promoter of maize plant have been investigated as a promoter useful for transformation of monocot plants. Among them, Act1 and Ubi1 promoters exhibit relatively a high activity in monocot plants as compared to CaMV 35S promoter, and therefore, have been generally used for transformation of monocot plants. However, Ubi1 promoter exhibits activity in numerous types of cells but does not cover the whole tissues of a plant body. Moreover, although Ubi1 promoter exhibits a strong activity especially in young roots, its activity is greatly reduced as the roots grow. In addition, Act1 promoter exhibits activity mainly in the elongating tissues and reproductive tissues. Thus, said promoters are not effective for expression of a ubiquitous gene in monocot plants.

Therefore, there exists a continuous necessity for developing a promoter showing a strong, stable and ubiquitous activity in transforming monocot plants.

SUMMARY OF THE INVENTION

According to the present invention, a rice plant was transformed with a recombinant plasmid containing a promoter for rice cytochrome c gene (OsCc1) and sgfp gene encoding a transformed green fluorescent protein, and the expressed fluorescent protein was then analyzed; as a result, it was identified that OsCc1 promoter can strongly, stably and ubiquitously induce the expression of a foreign gene in all the tissues of the rice plant. Therefore, OsCc1 promoter can be very effectively used for transformation of monocot plants.

DETAILED DESCRIPTION OF THE INVENTION

Figure 1A:
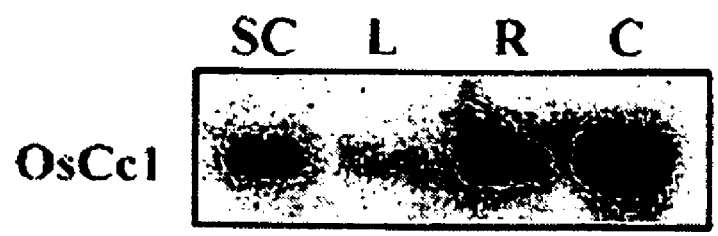
FIGS. 1a, 1b and 1c are photographs showing the results of Nothern blot analysis using total RNAs extracted from various tissues of an untreated rice plant, various tissues of a rice plant treated with $Bt_2cAMP$, and leaves of young seedlings treated with light, respectively.

Technical Field to which the Invention Belongs and the Prior Art in this Field

The present invention relates to a promoter for transformation of monocot plants. More specifically, the present invention relates to a process for varying a trait of monocot plants which comprises steps of transforming a monocot plant with a recombinant plasmid containing OsCc1 promoter for transformation of monocot plants and a desired foreign gene and of expressing said foreign gene.

Technical Subject to be Accomplished by the Invention

In response to said necessity in this technical field, the present inventors have taken a strong effort to develop a promoter effective for transformation of monocot plants. As a result, we have identified that when a rice plant is transformed with a recombinant plasmid containing a promoter for rice cytochrome c gene (OsCc1) and sgfp gene coding for a transformed green fluorescent protein and then the expressed fluorescent protein is analyzed, the fluorescent protein is strongly, stably and ubiquitously expressed in the whole tissues of the rice plant, and accordingly, we came to complete the present invention.

Therefore, the main purpose of the present invention is to provide OsCc1 promoter for transformation of monocot plants.

Another purpose of the present invention is to provide a process for varying a trait of monocot plants, which comprises transforming a monocot plant with a recombinant plasmid containing OsCc1 promoter.

[Constitution of the Invention]

In order to develop a promoter effective for transformation of monocot plants, the present inventors have first paid attention to cytochrome c. Cytochrome c is a small protein located in mitochondria of eukaryotes, and functions as a catalyst for transfer of electrons between the respiratory complexes III and IV. Up to now, cytochrome c has been extensively used for molecular evolutionary studies because its amino acid sequences and base sequences are highly preserved even among the organisms distantly related such as yeasts, mammals and plants. Further, it has also been used as a molecule useful for a protein targeting into organelles because of its unique subcellular location. Recently, cytochrome c has attracted a keen attention because its release into cytosol is an indicator of apoptosis in human cells. However, little is known in plants about cytochrome c except that *Arabidopsis* and rice cytochrome c genes (OsCc1) were cloned and sequenced (see, Kemmerer et al., *Mol. Biol. Evol.*, 8:212–226, 1991).

Thus, the present inventors have expected that since cytochrome c is involved in the electron transfer to play a role of supplying energy to cells, cytochrome c gene would be expressed at a high level in cells, and continuously and stably expressed in the whole tissues of individuals regardless of the development stage. Accordingly the inventors intended to develop OsCc1 promoter in the form of a promoter which can induce expression of said gene at a high level in the whole tissues of a plant body. Particularly, since in most cases promoters utilized for transformation of plants cannot be commonly used in dicot plants and monocot plants, they should be independently developed in both plants. However, at present the promoters which can be used for monocot plants are very limited, such as, Ubi1 and Act1 promoters, etc., and therefore, we have put the main emphasis on the development of OsCc1 promoter in the form of a promoter effective for transformation of monocot plants.

Hereinafter, the present invention will be more specifically explained.

The present invention provides a process for varying a trait of monocot plants which comprises steps of transforming a monocotyledon with a recombinant plasmid containing OsCc1 promoter for transformation of monocot plants and a desired foreign gene and of expressing said foreign gene. In this process, the foreign gene may be all the genes which are intended to be expressed at a high level in the whole tissues of a plant body, including selective marker genes comprising hygromycin-resistant gene $Hyg^R$ and herbicide-resistant gene bar or genes resistant to biological or non-biological stresses. The monocot plants include rice, barley, wheat or maize plants; and the transformation can be accomplished by particle bombardment method or *Agrobacterium*-mediated method.

The present inventors first conducted Nothern blot analysis for a total RNA extracted from respective tissues of a rice plant to analyze expression pattern of OsCc1 gene; constructed a recombinant plasmid containing OsCc1 promoter and sgfp gene coding for transformed green fluorescent protein; transformed a rice plant with said recombinant plasmid via *Agrobacterium*-mediated method; then, conducted Southern blot analysis and Western blot analysis using the gene and the protein extracted from the transformed rice plant, respectively; and analyzed the fluorescent image of the rice plant to determine the activity of OsCc1 promoter. It has been known that since OsCc1 promoter of animals contains CRE-binding site (cAMP response element binding site), its activity is greatly influenced by the concentration of cAMP; rbcS promoter having a high activity specifically in chloroplast is greatly influenced by light due to its unique properties; and OsCc1 promoter of a rice plant contains the base sequence similar to that of CRE-binding site. Therefore, said Nothern blot analysis was conducted to determine whether OsCc1 promoter which leads the expression of OsCc1 gene is influenced by cAMP or light. The activity of OsCc1 promoter was compared with the activities of Act1, rbcS and Ubi1 promoters, which are currently practically used for transformation of monocot plants.

The present invention will be more specifically illustrated through the following examples. A person having an ordinary knowledge in this technical field can clearly understand that these examples are intended only to specifically explain the present invention and the scope of the present invention is not limited to these examples in any manner.

EXAMPLE 1

Expression Pattern of OsCc1 gene

In order to investigate the expression pattern of OsCc1 gene, a total RNA was extracted from the respective tissues and cells of a rice plant by guanidinium/LiCl method and then subjected to Nothern blot analysis. First, embryogenic calli of a rice plant were obtained from embryo of mature *Oryza sativa* L. (cv *Nakdong*) and then maintained in MS solid medium, pH 5.8, containing 1% (w/v) agarose, 30 g/L sucrose and 2.5 mg/L 2,4-D. Said embryogenic calli were incubated in AA liquid medium containing 30 g/L sucrose, 2.0 mg/L 2,4-D and 0.2 mg/L kinetin using a shaking incubator at 120 rpm and in the dark at 26 to obtain suspension cultured cells. Rice plants, suspension cultured cells and calli, with or without treatment by 1 mM dibutyl cAMP ($Bt_2$cAMP, Sigma, USA) or by light, were frozen in liquid nitrogen. About 0.1 g of leaves, roots, calli and young seedlings were homogenized in 1 ml of extraction buffer solution containing 4 M guanidinium isothiocyanate, 25 mM sodium citrate (pH 7.0), 0.5% (w/v) sarcosyl and 0.1 M β-mercaptoethanol, then added 0.1 ml of 2 M sodium acetate (pH 4.0), 1 ml of water-saturated phenol (pH 4.5) and 0.2 ml of chloroform:isoamyl alcohol (1:1, v/v), well mixed together for 30 seconds and centrifuged at room temperature for 10 minutes at 5,000 g. The equal volume of isopropanol was added to the supernatant obtained from centrifuge, and then the mixture was allowed to stand for one hour at −20, thereafter centrifuged at 4 for 10 minutes at 10,000 g, washed with 70% (v/v) ethanol and dried. The resulting RNA pellet was dissolved in 40 ml of DEPC (diethyl pyrocarbonate)-treated water and the concentration of RNA was calculated from $A_{260}$ value. Then, Nothern blot analysis was conducted using 20 μg of total RNA according to the method of Sambrook, et al., (see, Sambrook J. et al., *Molecular Cloning: A Laboratory Manual*, $2^{nd}$ Ed., Cold Spring Harbor Laboratory Press, 1989). RNA transferred to the membrane was hybridized to [$^{32}$P]-probe present in a random primer labeling kit (Takara, Japan), washed and then analyzed by a phospho-image analyzer (FLA 3000, Fuji, Japan).

Figure 1B:
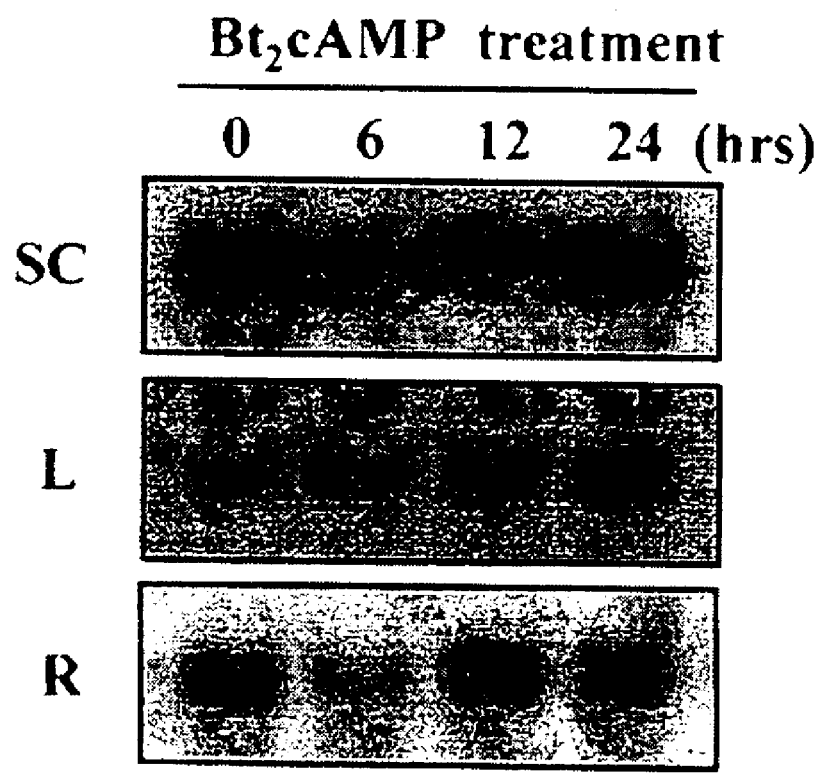
Figure 1C:
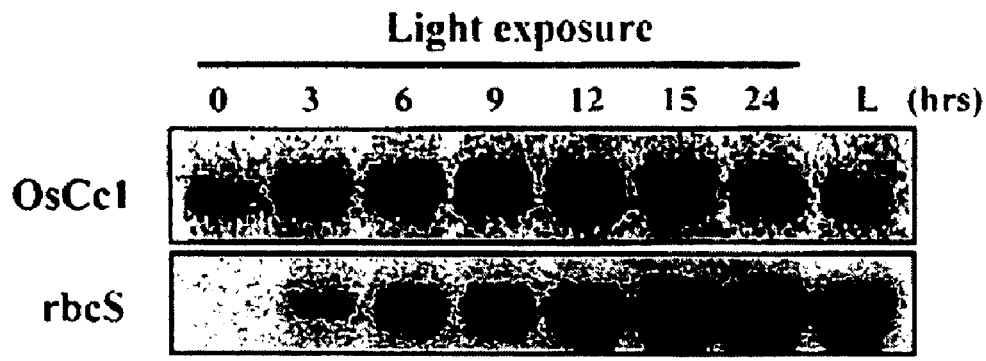

FIGS. 1*a*, 1*b* and 1*c* are photographs showing the results of Nothern blot analysis for total RNAs extracted from various tissues of untreated rice plant, from various tissues of rice plant treated with $Bt_2$cAMP, and from leaves of young seedlings treated with light, respectively. In FIGS. 1*a* and 1*b*, the symbols SC, L, R and C represent suspension cultured cells, leaves, roots and callus, respectively; the numerical values in FIGS. 1*b* and 1*c* represent the times during which the test samples were treated with $Bt_2$cAMP or light; and the symbol L in FIG. 1c represents mature leaves. As can be seen from FIGS. 1a, 1b and 1c, OsCc1 was expressed at a high level in suspension cultured cells, roots and callus, but at a relatively low level in leaves, and further the expression of OsCc1 was not influenced by cAMP or light. Therefore, it can be said that OsCc1 is independent on cAMP or light and is expressed in non-photosynthetic tissues at a higher level than in photosynthetic tissues. This result is consistent with the fact that chloroplast functions to supply major energy in photosynthetic tissues whereas mitochondria does in non-photosynthetic tissues.

EXAMPLE 2

Construction of Plasmid

Plasmids containing promoter of OsCc1, Act1 or Ubi1 and sgfp gene coding for transformed green fluorescent protein were constructed. 1.8 kb of OsCc1 promoter (SEQ. ID. No. 1) was PCR amplified from pOsCc1 (see, Kemmerer EC. et al., *Mol. Biol. Evol.*, 8:212–226, 1991) using the following two primers a and b containing XhoI or NcoI restriction site (indicated by underline):

5'-AA<u>CTGGAG</u>GAATTCGGATCTTCGAAGGTAGGC-3';

primer a (SEQ. ID. No. 2) and

5'-AA<u>CCATGG</u>CCGCCGCCGCCGCGAGAACG-3'; primer b (SEQ. ID. No. 3).

The amplified DNA was digested with XhoI and NcoI and then ligated to pBluescript KSII (see, Chiu W-L, et al., *Curr. Biol.*, 6:325–330, 1996) containing sgfp gene digested with the same restriction enzymes to construct plasmid pKSCG. Thereafter, the 2.5-kb DNA fragment containing the OsCc1-sgfp was obtained by digestion of pKSCG with XhoI and NotI, and ligated to pSB 105 (see, Jang, I-C. et al., *Mol. Breeding*, 5:453–461, 1999) digested with the same restriction enzymes to produce the plasmid pSB-CG (OsCc1-sgfp). pSB 105 contains potato protease inhibitor II gene terminator, $^{35}$S promoter, bar gene (phosphinothricin acetyltransferase gene) and nopaline synthase gene terminator between the right-border sequence and the left-border sequence of pSB11. Phosphinothricin acetyltransferase encoded by bar gene plays a role of detoxifying phosphinothricin-based herbicides and therefore, can serve as a selective marker. Then, the DNA fragment was obtained by digestion of pSK-RG (see, Chiu W-L, et al., *Curr. Biol.*, 6:325–330, 1996), containing rbcS promoter linked to sgfp gene, with BamHI and NotI, and ligated to pSB105 digested with the same restriction enzymes to produce the plasmid pSB-RG (rbcS-sgfp). Thereafter, the rbcS promoter in the resulting plasmid pSB-RG was replaced with Act1 promoter of rice (see, McElroy D. et al., *Mol. Gen. Genet.*, 231:150–160, 1991) to produce plasmid pSBG700 (Act1-sgfp).

Figure 2:
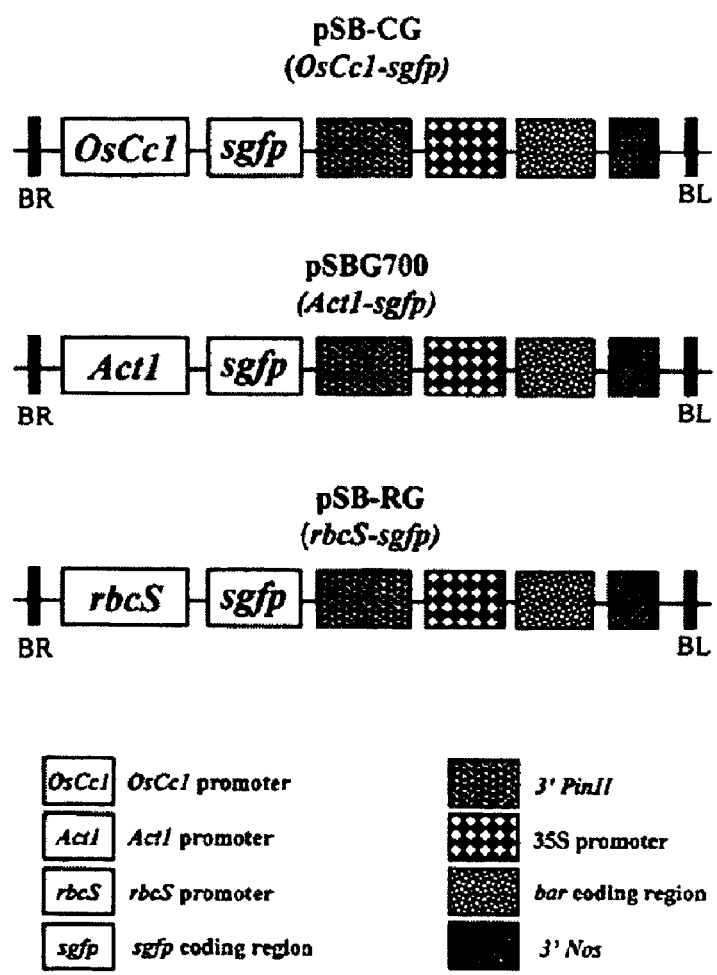
FIG. 2 shows gene maps of plasmids pSB-CG, pSB-RG and pSBG700.

FIG. 2 is the drawing showing the gene maps of plasmids pSB-CG, pSB-RG and pSBG700. In FIG. 2, BR and BL represent the right border and the left border, respectively; and 3'PinII and 3' Nos represent terminators of potato protease inhibitor II gene and of nopaline synthase gene, respectively. Plasmids pSB-CG, pSB-RG and pSBG700 constructed as above were respectively introduced into *Agrobacterium tumefaciens* LBA4404 by triparental mating.

EXAMPLE 3

Stability of Transgene in a Rice Plant Produced by *Agrobacterium*—Mediated Transformation To about 200 non-trashed grains (*Oryza sativa* L. cv *Nakdong*) was added 70% (v/v) ethanol and slightly mixed for one minute to sterilize the grains. Next, ethanol was discarded and the residual grains were slightly mixed with 100 ml of 20% (v/v) CLOROX for one hour to further sterilize the grains, which were then washed several times with sterilized water. In order to transform a rice plant, callus induction, co-cultivation with *Agrobacterium* containing the plasmid as prepared in the above example and selection of transformed callus were conducted according to the method described by Jang, et al. (see, Jang, I-C. et al., *Mol. Breeding*, 5:453–461, 1999). The rice plant transformed by *Agrobacterium*-mediated method was grown in a greenhouse to select only the rice plant having a resistance to herbicide. By Southern blot analysis of the genome of the transgenic rice plant as transformed and selected as above, it was identified that transduced transgene was integrated into chromosome of the rice plant and had 1 to 3 copies. In view of the fact that a rice plant was identified as containing a single copy of OsCc1 in its genome by genomic DNA hybridization, we could easily expect that the transgene would be stably located in a plant body and expressed at a high level.

EXAMPLE 4

Activity of Promoters in the Respective Tissues of a Transformed Rice Plant

By analysis of fluorescent proteins expressed in the respective tissues of a rice plant transformed with plasmids pSB-CG, pSB-RG and pSBG700 constructed as above, the activities of the respective promoters were analyzed and compared with each other.

EXAMPLE 4-1

Western Blot Analysis of Fluorescent Proteins

Figure 3:
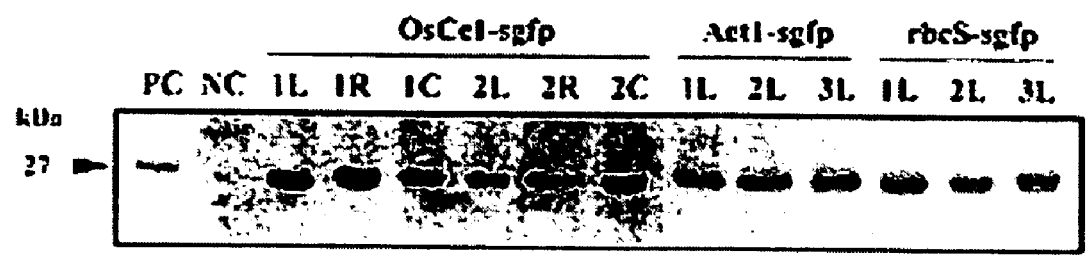
FIG. 3 is a photograph showing the result of Western blot analysis for proteins extracted from various tissues of a transformed rice plant.

Proteins were extracted from the respective tissues of a transformed rice plant and then subjected to Western blot analysis using sGFP antibody. About 0.1 g of callus, leaf and root tissues of a rice plant were ground in liquid nitrogen, homogenized in buffer solution containing 20 mM Tris-HCl (pH 8.0), 10 mM EDTA, 30 mM NaCl and 2 mM phenylmethanesulfonyl fluoride at 4 for one hour, and then centrifuged at 4 for 5 minutes. The concentration of protein contained in the supernatant was determined using Bradford solution (Bio-Rad, USA). Crude protein was electrophoresed on 15% SDS-polyacrylamide gel, electroblotted to polyvinylidene difluoride (PVDF) by means of Semidry apparatus (Bio-Rad, USA), and then subjected to immunoblot analysis using sGFP polyclonal antibody (Clontech, USA) and the secondary antibody conjugated with alkaline phosphatase. FIG. 3 is the photograph showing the result of Nothern blot analysis for proteins extracted from the respective tissues of a transformed rice plant. Proteins were extracted from 2, 3 or 3 plants selected from rice plants transformed with OsCc1-sgfp, Act1-sgfp or rbcS-sgfp, respectively, and then analyzed. In FIG. 3, the symbols L, R and C, PC and NC represent proteins extracted from leaves, roots, callus, purified sGFP, and leaves of untransformed rice plant, respectively, and the respective numerical values denote the number of selected individuals. From FIG. 3, it could be seen that sGFP is expressed in all the tissues of a rice plant transformed with OsCc1-sgfp at a high level, which is similar to those in rice plants transformed with Act1-sgfp or rbcS-sgfp.

EXAMPLE 4-2

Fluorescent Analysis of sGFP in a Transformed Rice Plant

Figure 4A:
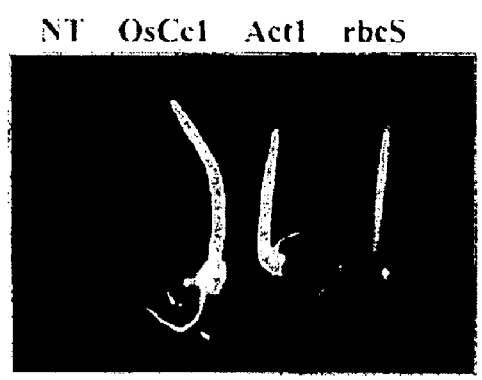
FIG. 4a is a photograph showing sGFP fluorescent images of young seedlings transformed with OsCc1-sgfp (OsCc1), Act1-sgfp (Act1) or rbcS-sgfp (rbcS)
Figure 4B:
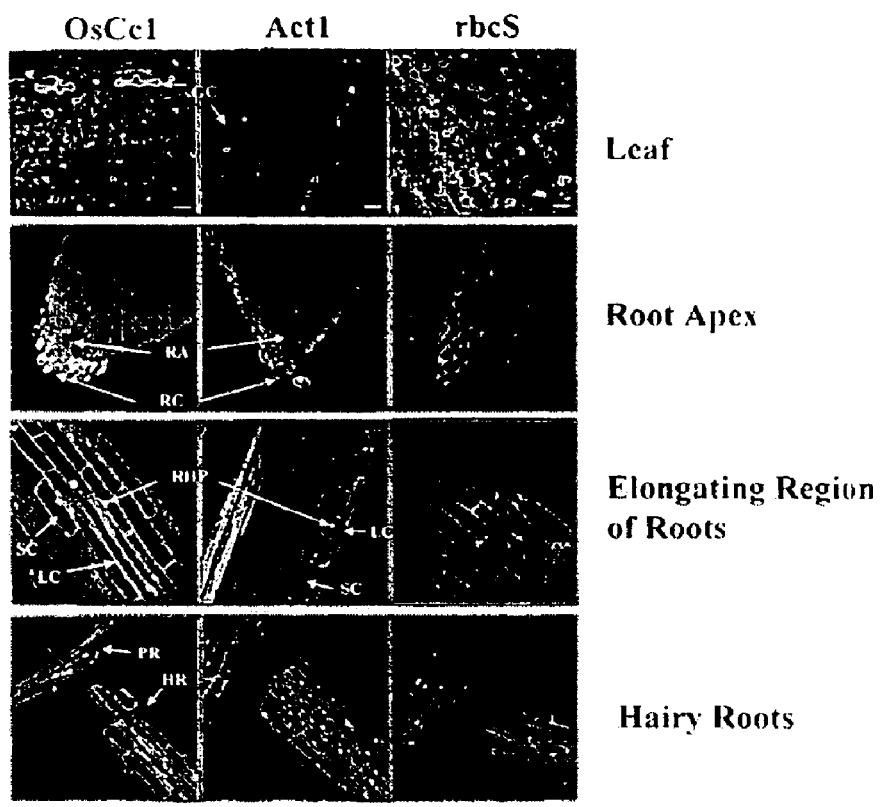
FIG. 4b shows photographs of sGFP fluorescent images of various tissues of rice plants transformed with OsCc1-sgfp (OsCc1), Act1-sgfp (Act1) or rbcS-sgfp (rbcS)
Figure 4C:
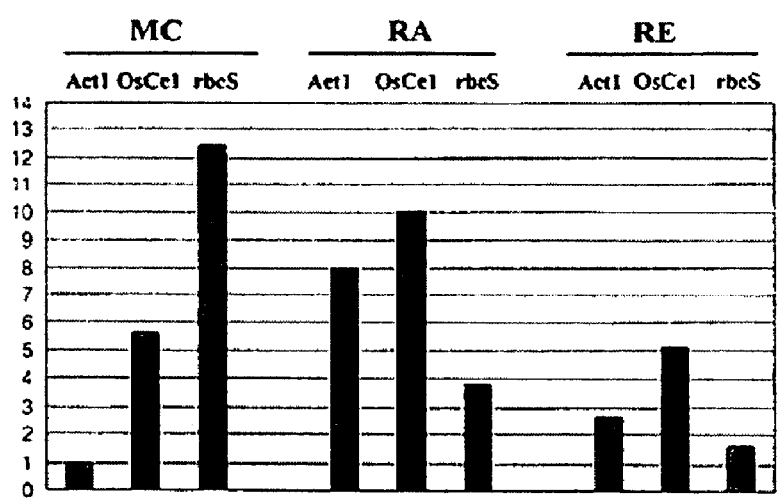
FIG. 4c shows graphs of relative sGFP fluorescent intensity of various tissues of rice plants transformed with OsCc1-sgfp (OsCc1), Act1-sgfp (Act1) or rbcS-sgfp (rbcS).

In order to examine the activity of OsCc1 promoter at the level of the whole plant, the transformed seeds and the untransformed seeds were grown to analyze the fluorescence of sGFP in a rice plant. A high-resolution CCD color video camera (Model CoolSNAP, Roper Scientific Inc., USA) utilizing a digital video imaging system was used to collect sGFP fluorescent images of young seedlings, transformed with OsCc1-sgfp (OscC1), Act1-sgfp (Act1) or rbcS-sgfp (rbcS), in a perpendicular position. The result obtained is shown in FIG. 4a. In addition, sGFP fluorescent images in leaves, root apexes, elongating regions of roots and hairy roots of the respective transformed rice plants were observed with confocal laser scanning microscopy (Carl Zeiss LSM510, Carl Zeiss, Germany). The observation result is shown in FIG. 4b. The intensity of sGFP fluorescence observed in FIG. 4b was calculated by means of a software equipped in LSM510 version 2.8 and the relative fluorescent intensity thereof, which was calculated on the basis of the value of the fluorescent intensity of MC developed by Act1 activity to be fixed as 1, is shown in FIG. 4c. In FIG. 4a the symbol NT represents untransformed young seedlings; in FIG. 4b the symbols GC, RA, RC, RHP, LC, SC, PR and HR represent guard cells, root apexes, root caps, hair protuberances of root, long cells, short cells, primary roots and hairy roots, respectively (where the scale bar represented by the white line has a length of 30 $\mu$m); and in FIG. 4c the symbols MC, RA and RE represent mesophyll cells, root apexes and elongating regions of roots, respectively.

From FIG. 4a, it could be seen that untransformed young seedlings(NT) do not show any fluorescence whereas transformed young seedlings (OsCc1, Act1 and rbcS) exhibit light green fluorescence and particularly, OsCc1 exhibits fluorescence in whole tissues of the plants. In addition, from FIG. 4b, in leaf cells, it could be seen that plants transformed with OsCc1-sgfp exhibit sGFP fluorescence at a higher level than plants transformed with Act1-sgfp but at a lower level than plants transformed with rbcS-sgfp. In root cells, it could be seen that plants transformed with OsCc1-sgfp or Act1-sgfp exhibit sGFP fluorescence at a higher level than plants transformed with rbcS-sgfp, and particularly, plants transformed with OsCc1-sgfp exhibit brighter fluorescence in root apex, root cap and hair protuberance of roots. Therefore, it can be regarded that OsCc1 promoter exhibits the activity in the whole tissues of a plant body and particularly, displays a higher activity in rapidly dividing cells and cells having a high metabolic activity. Such result could also be identified from FIG. 4c. The following Table 1 shows the activities of OsCc1 promoter and the promoters which are widely used for transformation of rice plants. In Table 1, 35S and 35Si denote intron-free CaMV 35S promoter and CaMV 35S promoter conjugated with intron of maize Adh1 promoter, respectively; Adh1, Ubi1 and Act1 denote promoters conjugated with their intrinsic introns, respectively; and OsCc1 and rbcS denote intron-free rice promoters. The values shown in the table is a relative value calculated on the basis of the value of the activity of CaMV 35S or Act1 to be fixed as 1. From Table 1, it could be seen that the activity of OsCc1 promoter in leaves and roots is higher than that of Act1 promoter by 5 and 2 times, respectively.

TABLE 1

Activities of OsCc1 promoter and the promoters which are widely used for transformation of rice plants

| Analysis | 35S | 35Si | Adh1 | Ubi1 | Act1 | rbc1 | OsCc1 | Remarks |
|---|---|---|---|---|---|---|---|---|
| Temporary analysis[a] | 1 | 4.2 | 4 | ND | 22 | ND | ND | M |
| Temporary analysis[b] | ND | 1 | 1.5 | 10 | 1.5 | ND | ND | C |
| Leaves of transgenic plant | ND | ND | ND | ND | 1 | 5 | ND | J |
| Leaves of transgenic plant | ND | ND | ND | ND | 1 | 12 | 5 | I |
| Roots of transgenic plant | ND | ND | ND | ND | 1 | 0.5 | 2 | I |

Notes)
[a]protoplast which originated from suspension cultured cells
[b]protoplast which originated from callus cells
M: McElroy D. et al., Mol. Gen. Genet., 231: 150–160, 1991
C: Cornejo M-J. et al., Plant Mol. Biol., 23: 567–581, 1993
J: Jang I-C, et al., Mol. Breeding, 5: 453–461, 1999
I: the present invention
ND: the value is not determined.

Thus, while the invention has been particularly shown and described with respect to preferred examples thereof, it will be understood by those skilled in the art that changes in forms and details may be made therein without departing from the scope and spirit of the invention.

What is claimed:

1. An isolated OsCcl promoter of SEQ ID NO:1 for transformation of monocot plants.

2. A process for varying a trait of a monocot plant, wherein the process comprises transforming a monocot plant with a recombinant plasmid containing an OsCcl promoter operably linked to a desired isolated nucleic acid sequence, whereby a trait of a monocot plant is varied.

3. The process for varying trait of a monocot plant according to claim 2, wherein the isolated nucleic acid sequence is a selective marker gene comprising $Hyg^R$ and bar, or provides resistance to biological or non-biological stresses.

4. The process for varying a trait of a monocot plant according to claim 2, wherein the monocot plant is a rice, barley, wheat or maize plant.

5. The process for varying a trait of a monocot plant according to claim 2, wherein transforming is accomplished by a particle bombardment or is *Agrobacterium*-mediated.

* * * * *